United States Patent
Breitenbach et al.

(10) Patent No.: US 6,231,848 B1
(45) Date of Patent: *May 15, 2001

(54) TOPICAL PRODUCTS AS PROPHYLACTIC OF CURATIVE AGENTS FOR BACTERIAL SKIN INFECTIONS

(75) Inventors: Jörg Breitenbach, Mannheim; Bernhard Fussnegger, Kirrweiler; Siegfried Lang, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/269,333

(22) PCT Filed: Sep. 26, 1997

(86) PCT No.: PCT/EP97/05291

§ 371 Date: Mar. 25, 1999

§ 102(e) Date: Mar. 25, 1999

(87) PCT Pub. No.: WO98/14199

PCT Pub. Date: Apr. 9, 1998

(30) Foreign Application Priority Data

Sep. 30, 1996 (DE) .............................. 196 40 364

(51) Int. Cl.⁷ .............................. A61K 47/32; A61K 7/20; A61K 33/38
(52) U.S. Cl. .................. 424/78.24; 424/617; 424/618; 424/615
(58) Field of Search .................. 424/78.24, 617, 424/618

(56) References Cited

U.S. PATENT DOCUMENTS

| | | |
|---|---|---|
| 2,040,806 * | 5/1936 | Feigl .................. 424/618 |
| 3,376,110 | 4/1968 | Shiraeff . |
| 3,480,557 | 11/1969 | Shiraeff . |
| 4,451,582 | 5/1984 | Denzinger et al. . |
| 4,567,036 | 1/1986 | Simon et al. . |
| 4,592,489 | 6/1986 | Simon et al. . |
| 4,646,730 | 3/1987 | Schonfeld et al. . |
| 5,077,047 | 12/1991 | Biss et al. . |
| 5,094,867 | 3/1992 | Detering et al. . |
| 5,108,742 | 4/1992 | Merianos . |
| 5,130,124 | 7/1992 | Merianos et al. . |
| 5,364,601 | 11/1994 | Salpekar . |
| 5,437,858 * | 8/1995 | Hungerbach et al. .......... 424/618 |
| 5,575,995 * | 11/1996 | Giovanni ..................... 424/78.24 |
| 5,945,032 * | 8/1999 | Breitenbach et al. ......... 424/78.24 |

FOREIGN PATENT DOCUMENTS

| | | |
|---|---|---|
| 92/17158 | 10/1992 | (WO) . |
| 93/00884 | 1/1993 | (WO) . |

OTHER PUBLICATIONS

Nowak, *Die kosmetischen Praeparate*, vol. 1, 1982, 202–223.
Smith, *SOFW Journal*, 121, Jan. 14, 1995, 1013–1017.
Horn et al., *J. of Pharm. Sci.*, 71(9), 9/82, 1021–1026.
Hirai et al., *Makromol. Chem. Rapid. Commun.*, vol. 5, 1984, 381–384.
Esumi et al., *J. of App. Poly. Sci.*, vol. 44, 1992, 1003–1007.
Hirai, *J. Macromol. Sci.–Chem.*, A13 (5), 1979, 633–649.
Wang et al., *Polymer Bull.*, 25, 1991, 139–144.
Fickentscher, *Cell. Chem.*, 13, 1932, 58–64, 71 and 74.
Rompp, *Chemie Lexikon*, 9th Ed., "Popcorn Polymerisate", p. 3586.
*Ency. of Poly. Sci. and Eng.*, vol. 17, 1989, 212–213.
*Ency. of . Poly. Sci. and Eng.*, vol. 13, 1988, 453–463.

* cited by examiner

*Primary Examiner*—Peter F. Kulkosky
(74) *Attorney, Agent, or Firm*—Keil & Weinkauf

(57) ABSTRACT

The present invention relates to topical products intended for use as prophylactic or curative agents for bacterial skin infections, containing at least one polymeric complex substantially consisting of hydrogen peroxide, a suitable polymer for the complex formation thereof, possibly another bactericidal compound and possibly a metal salt or a metal colloid.

14 Claims, No Drawings

TOPICAL PRODUCTS AS PROPHYLACTIC OF CURATIVE AGENTS FOR BACTERIAL SKIN INFECTIONS

The present invention relates to topical compositions for the prophylaxis and treatment of bacterial infections of skin which comprise at least one polymer complex which is essentially composed of hydrogen peroxide, a polymer suitable for complex formation with hydrogen peroxide, with or without another bactericidal compound, and with or without a metal salt or metal colloid.

The bactericidal action of hydrogen peroxide is utilized in a variety of ways for the disinfection of liquids and articles and for the topical therapy of infectious diseases in human and veterinary medicine. It can be used topically in the form of liquid preparations, for example aqueous solutions for irrigating body cavities or fistulas, in the form of solid preparations, e.g. as complexes of hydrogen peroxide with urea, or in the form of salts or compounds which form hydrogen peroxide on hydrolysis or decomposition. The bactericidal action of such preparations extends to Gram-positive and Gram-negative cocci, bacilli or spirochetes, and to a number of yeasts and fungi. In addition, hydrogen peroxide is also used, because of its cleansing and hemostatic action, for viral infections and inflammations not caused by microorganisms.

However, the use of hydrogen peroxide is restricted in principle by its tendency to decompose on exposure to heat or light or in the presence of impurities such as dust, various metal salts and alkaline substances. Although its bactericidal action derives from these decomposition reactions, there are limitations on the storability and utilizability of its preparations because the hydrogen peroxide content decreases.

It has emerged that hydrogen peroxide can be stabilized in the form of complexes with polymers, preferably polyvinylpyrrolidones. Complexes of this type are described, for example, in U.S. Pat. No. 3,376,110, U.S. Pat. No. 3,480,557, U.S. Pat. No. 5,077,047, U.S. Pat. No. 5,108,742, WO-A 91/07184 and WO-A 92/17158. These complexes are, as a rule, stable powders which are easy to handle and can be incorporated into a large number of preparations. Their use for the treatment of acne vulgaris is described in U.S. Pat. No. 5,130,124. These complexes may have the disadvantageous effect that the release of hydrogen peroxide depends on the strength of binding to the polymer, but its action depends on its decomposition and thus on the decomposition catalysts present in the system (dust particles, basic impurities, traces of metals).

It is often necessary, for comprehensive therapy of bacterial infections of skin, to combine the bactericidal action of hydrogen peroxide with other therapeutic effects. Thus, in the cosmetic treatment of acne there is often use of keratolytic substances such as salicylic acid or sulfur (see G. A. Novak in "Die kosmetischen Präparate", Volume 1, Verlag f ür chemische Industrie, Augsburg, 1982, pages 202 ff) or vitamin A acid. It is furthermore known that α-hydroxy carboxylic acids have a keratolytic effect (see W. Smith, S ÖFW-Journal, 121 (1995)1013 ff). However, said substances may result in skin irritation, erythema or allergies, and less commonly in severe inflammatory reactions. On the other hand, it is known that α-hydroxy acids or salicylic acid form complexes with polyvinylpyrrolidone (see D. Horn and W. Ditter, J. Pharm. Sci. 71, 1982, 1021 ff).

It is furthermore known that polyvinylpyrrolidone can be employed as protective polymer for metallic colloid solutions, for example of copper, silver (Hirai et al., Makromol. Chem. Rapid Commun. 5 (1984) 381), palladium, gold, rhodium or platinum. Esumi et al. describe the preparation of colloidal silver solutions in the presence of vinyl alcohol and N-vinylpyrrolidone (J. Appl. Polym. Sci. 44 (1992) 1003) or polyvinylpyrrolidone homopolymers (Hirai et al. J. Macromol. Sci. Chem. A13 (1979) 633). Bimetallic colloids have also been described, especially for use as catalysts, by Wang et al. (Polymer Bulletin 25 (1991) 139).

It is furthermore known that silver ions in the form of silver salts represent toxicologically acceptable antiseptics with a broad spectrum of action. Thus, 1% strength silver nitrate solution is, in Credé's method (prevention of gonoblennorrhea), administered into the conjunctival sac of neonates immediately after birth.

It is an object of the present invention to provide a topical composition for the treatment of bacterial or viral infections of the skin which, on the one hand, ensures a controlled effect of the bactericidal ingredient and, at the same time, shows other therapeutically worthwhile effects without the prior art disadvantages.

We have found that this object is achieved by polymer-bound hydrogen peroxide, where another therapeutically active substance is additionally bound in the polymer, with or without a metal colloid or metal salt.

The present invention therefore relates to a composition for the prophylaxis or treatment of bacterial or viral infections of skin, comprising at least one polymer complex which is essentially composed of a) hydrogen peroxide b) at least one polymer suitable for binding the hydrogen peroxide, c) with or without another therapeutically active compound and d) with or without a metal colloid or metal salt with the proviso that the polymer complexes comprise at least one of components c) or d).

$C_1$–$C_n$-alkyl means hereinafter linear, branched or cyclic alkyl groups with 1 to n carbon atoms. Examples are methyl, ethyl, n-propyl, i-propyl, n-butyl, 2-butyl, i-butyl, t-butyl, n-hexyl, 2-hexyl, 2-ethylhexyl or n-decyl, cyclopentyl or cyclohexyl. $C_1$–$C_n$-alkylene means linear or branched alkylene units, for example methylene, ethylene, ethylidene, 1,1-, 1,2-, 1,3-, 2,2-propylene, 1,1-, 1,2-, 1,3-, 1,4-, 2,2-, 2,3-butylene. Aryl groups are phenyl or naphthyl which are unsubstituted or substituted by 1 to 3 $C_1$–$C_4$-alkyl groups or halogen atoms.

The polymeric component b) of the polymer complexes present in the composition according to the invention is preferably a homo- or copolymer of one or more N-vinyllactams. Preferred N-vinyllactams are N-vinylpyrrolidone, N-vinylpiperidone, N-vinylcaprolactam, N-vinyl-3-morpholinone, N-vinyl-4-oxazolidinone and mixtures thereof. Particularly suitable comonomers are N-vinylheterocycles, e.g. vinylpyridines or vinylimidazoles, which may carry one or more $C_1$–$C_4$-alkyl radicals or phenyl radicals. Examples which may be mentioned are: N-vinylimidazole and 2-methyl-1-vinylimidazole, 4-methyl-1-vinylimidazole, 5-methyl-1-vinylimidazole, 2-ethyl-1-vinylimidazole, 2-propyl-1-vinylimidazole, 2-isopropyl-1-vinylimidazole, 2-phenyl-1-vinylimidazole, 2-vinylpyridine, 4-vinylpyridine and 2-methyl-5-vinylpyridine.

It is furthermore possible to employ $C_1$–$C_8$-alkyl vinyl ethers, e.g. methyl vinyl ether, ethyl vinyl ether, n-propyl vinyl ether, i-propyl vinyl ether, n-butyl vinyl ether, i-butyl vinyl ether, t-butyl vinyl ether, 2-ethylhexyl vinyl ether, vinyl esters of $C_1$–$C_{10}$-alkyl- or $C_6$–$C_{10}$-arylcarboxylic acids, e.g. vinyl acetate, vinyl propionate, vinyl butyrate, vinyl hexanoate, vinyl-2-ethylhexanoate, vinyl decanoate, vinyl laurate, vinyl stearate or vinyl benzoate. Also suitable are esters of acrylic acid or of methacrylic acid with $C_1$–$C_{12}$-alkanols, preferably $C_1$–$C_4$-alkanols. Examples thereof are methyl (meth)acrylate, ethyl (meth)acrylate, n-butyl (meth)acrylate. Further possible comonomers are conjugated $C_4$–$C_8$-dienes such as butadiene or isoprene, vinylaromatic compounds such as styrene, α-methylstyrene or vinyltoluenes and cationically modified vinyl monomers. Examples of the latter are monoethylenically unsaturated $C_3$–$C_5$-carboxylic esters with amino alcohols of the formula

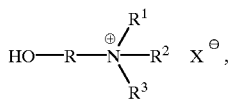

(I)

where R is $C_2$–$C_5$-alkylene, $R^1$, $R^2$ and $R^3$ are, independently of one another, H, $CH_3$, $C_2H_5$, $C_3H_7$, and $X^\ominus$ is an anion. Also suitable are amides of these carboxylic acids derived from amines of the formula

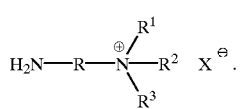

(II)

The substituents in formula II and $X^\ominus$ have the same meaning as in formula I. Examples of suitable carboxylic acids are acrylic acid, methacrylic acid, crotonic acid, maleic acid (anhydride), fumaric acid and itaconic acid. Suitable cationically modified vinyl monomers are also salts or quaternization products of N-vinylimidazole and 1-vinyl-2-methylimidazole.

The polymers used according to the invention comprise said N-vinyllactam units in amounts of more than 20%, preferably 30 to 99% and, in particular, 35 to 80% and the comonomers in amounts of up to 80%, preferably 1 to 70% and, in particular, 20 to 65% of the weight of the polymers.

These polymers may also comprise crosslinking monomer units in amounts of up to 20%, preferably up to 5% and, in particular, 0.1 to 3% of the weight of the polymer. Suitable crosslinkers are, as a rule, compounds having at least 2 non-conjugated ethylenic double bonds in the molecule. Examples thereof are N,N'-methylenebisacrylamide, polyethylene glycol diacrylates and polyethylene glycol dimethacrylates, trimethylolpropane triacrylate, trimethylolpropane trimethacrylate, ethylene glycol diacrylate, propylene glycol diacrylate, butanediol diacrylate, hexanediol diacrylate, hexanediol dimethacrylate, diacrylates and dimethacrylates of block copolymers of ethylene oxide and propylene oxide, polyhydric alcohols such as glycerol or pentaerythritol esterified twice or three times with acrylic acid or methacrylic acid, triallylamine, tetraallylethylenediamine, trimethylolpropane diallyl ether, pentaerythritol triallyl ether, N,N'-divinylethyleneurea and/or N,N'-divinylpropyleneurea. Also suitable as crosslinking monomers are divinylaromatic compounds such as divinylbenzene, but also dicyclopentadiene, vinyl (meth)acrylate, vinylnorlornene, tricyclodecenyl (meth)acrylate.

In a preferred embodiment, water-soluble polymers are employed. In this connection, "water-soluble" means that the polymers used according to the invention have a solubility at 20° C. of at least 0.5 g, preferably at least 2 g and, in particular, at least 5 g, in 100 g of water. Preferred comonomers in this case are vinyl acetate, vinyl propionate, methyl acrylate, ethyl acrylate, n-propyl acrylate, n-butyl acrylate, methyl methacrylate, ethyl methacrylate, acrylonitrile, methacrylonitrile and vinylimidazole. Copolymers of N-vinyllactams with one another are likewise suitable. Copolymers of N-vinylpyrrolidone and N-vinylcaprolactam, N-vinylpyrrolidone and vinyl acetate, and homopolymers of N-vinylpyrrolidone are particularly preferred. These water-soluble homo- and copolymers usually have Fikentscher K values (see Cellulose-Chemie 13 (1932) 48–64 and 71–94) in the range from 10 to 110, preferably 20 to 100.

The preparation of water-soluble polymers based on N-vinyllactams is described, for example, in DE-A 22 18 935 or the earlier application P 196 09 864.5. They are preferably prepared by free-radical solution polymerization in an aqueous or alcoholic solvent, for example in water, methanol, ethanol, i-propanol or mixtures thereof.

Particularly suitable initiators for the free-radical polymerization are those suitable for free-radical polymerization in aqueous solution. Those particularly suitable are aliphatic or cycloaliphatic azo compounds, e.g. 2,2'-azobis (isobutyronitrile), 2,2'-azobis(2-methylbutyronitrile), 2,2'-azobis(2,4-dimethylvaleronitrile), 1,1'-azobis(1-cyclohexanecarbonitrile), (2-carbamoylazo)isobutyronitrile, 4,4'-azobis(4-cyanovaleriic acid) and their alkali metal and ammonium salts, dimethyl 2,2'-azobis isobutyrate, 2,2'-azobis[2-(2-imidazolin-2-yl)propane], 2,2'-azobis(2-amidinopropane) and the acid addition salts of the two latter compounds. Further suitable initiators are hydrogen peroxide, hydroperoxides combined with suitable reducing agents or peroxo salts. Examples of suitable hydroperoxides are t-butyl hydroperoxide, t-amyl hydroperoxide, cumene hydroperoxide and pinane hydroperoxide, each combined with, for example, a salt of hydroxymethanesulfinic acid, an iron(II) salt or ascorbic acid. Particularly suitable peroxo salts are alkali metal peroxodisulfates. The amount of initiator used is in the range from 0.02 to 15 mol %, preferably 0.05 to 3 mol %, based on the monomers.

The polymerization is normally carried out at a neutral pH in the range from 5 to 9. If necessary, the pH is adjusted or maintained by adding a base such as ammonia or an acid such as HCl or a buffer system. If low molecular weights are required, the reaction can also be carried out in the presence of a compound which controls the molecular weight of the polymers. Examples thereof are aldehydes such as formaldehyde, acetaldehyde, propionaldehyde or allyl compounds such as allyl alcohol. It is also possible to employ regulators which contain sulfur in organically bound form. Examples thereof are butyl mercaptan, n-hexyl mercaptan, n-dodecyl mercaptan, water-soluble compounds such as bisulfites, disulfites, ethyl thioglycolate, cysteine, 2-mercaptoethanol, mercaptoacetic acid, 3-mercaptopropionic acid, thioglycerol, thiodiglycol, thiourea or dimethyl sulfoxide.

The resulting polymer solutions generally have solids contents in the range from 3 to 70% by weight, preferably 30 to 60% by weight. They can be employed for the process according to the invention as they result from the polymerization, without further isolation or treatment, or else be isolated as dry substance by precipitation or removal of the solvent.

In another preferred embodiment, insoluble polymers are employed. Polymers of this type are obtained by polymerizing the monomers in the presence of one of the above-mentioned crosslinkers. However, the polymers can also be crosslinked subsequently by physical effects such as radiation or by chemical reaction with a bi- or polyfunctional compound able to react with the functional groups present in the polymers, and can thus be rendered insoluble. Processes of this type are known to the skilled worker and described in the literature. Particularly preferred insoluble polymers are the popcorn polymers (Römpp, Chemie-Lexikon, 9th edition "Popcorn Polymerisate" and literature cited therein). The preparation of popcorn polymers is described, for example, in EP-A 88 964 and EP-A 438 713. As a rule, they are prepared by bulk, solution or precipitation polymerization of the monomers, preferably in the presence of small amounts of a crosslinker (0.1–4% of the weight of the monomers).

The polymer complexes used according to the invention may contain as other therapeutically active ingredients c) compounds selected from aldehydes, preferably dialdehydes, α-hydroxy carboxylic acids, arylcarboxylic acids, aryldicarboxylic acids, hydroxyarylcarboxylic acids or hydroxy-substituted aromatic compounds. Preferred substances are those tolerated on topical application of the pharmaceuticals. Examples of preferred aldehydes are glutaraldehyde or glyoxal. The α-hydroxy carboxylic acids preferably used are glycolic acid, lactic acid, hydroxyoctanoic acid, malic acid, pyruvic acid and citric acid. Examples of suitable aromatic carboxylic acids are benzoic acid, phthalic acid, isophthalic acid or terephthalic acid. Examples of suitable hydroxyarylcarboxylic acids are salicylic acid, 3-hydroxybenzoic acid, 4-hydroxybenzoic acid, 2,4-dihydroxybenzoic acid, 3,4-dihydroxybenzoic acid and 3,5-dihydroxybenzoic acid. As mentioned above, said compounds are presumably bound in a complex with the polymer.

The polymer complexes used according to the invention may contain as metal component d) a metal salt or metal colloid, preferably of copper, silver, gold, rhodium, iridium, palladium or platinum. Particularly preferred colloids or salts are those of copper or silver, especially of silver. Examples of suitable silver salts are silver nitrate, silver acetate, silver lactate, silver phosphate, silver chloride, silver bromide, silver hydroxide, silver carbonate, silver oxide, silver periodate or the sodium chloride/silver chloride complex ($Na[AgCl_2]$). Silver colloids can be obtained, for example, by treating aqueous solutions of a suitable silver salt with a reducing agent such as hydrogen, ascorbic acid, ribose, glucose, hydrazine, an aldehyde or an alcohol (see Römpp, Chemie-Lexikon, 9th edition "Kolloide").

The polymer complexes in the compositions according to the invention contain hydrogen peroxide in amounts of, as a rule, from 0.5 to 30%, preferably 5 to 23% and, in particular, 6 to 15% of the weight of the finished polymer complex. The polymer content is, as a rule, from 50 to 99.5%, preferably 74 to 95% and, in particular, 83 to 94% by weight. The content of other therapeutically active substances c) is in the range from 0 to 15% by weight, preferably 0.0005 to 10% by weight and, in particular, 0.01 to 3% by weight. The metal content in the polymer complexes is, as a rule, from 0 to 5% by weight, preferably 0.005 to 3% by weight and, in particular, 0.01 to 2% by weight.

The polymer complexes can be prepared in a variety of ways depending on the nature of the polymers used and on ingredients c) and d). When soluble polymers are used, spray drying or spray granulation has proven suitable. This entails preferably aqueous solutions of the polymers being spray dried or granulated together with solutions of hydrogen peroxide and with solutions of active substances c) and/or of metal salts or dispersions of the metal colloids (component d) using multicomponent nozzles. The solutions may also have been mixed beforehand. It is also possible to employ hydrogen peroxide solutions stabilized by metal salts or colloids. In another variant, a metal colloid is deposited from an aqueous solution by one of said reducing agents in the presence of a polymer. There have been reports in the literature (see above) on the deposition of metal colloids in the presence of vinylpyrrolidone polymers. The resulting dispersion is then spray dried together with a hydrogen peroxide solution. The solutions can be mixed beforehand in this case too. The polymer solutions used can be prepared by dissolving the polymer in a suitable solvent, preferably an aqueous alcoholic or aqueous solvent. It is also possible to use the solutions resulting from the polymerization directly. Hydrogen peroxide is employed in the form of 30 to 70% by weight, preferably 30 to 60% by weight, aqueous solutions in the process according to the invention.

Processes of spray drying or spray granulation are known to the skilled worker. The solid polymer complexes can be obtained in spray towers of conventional design in the present case too. The drying gases used are inert gases, for example nitrogen, which are passed countercurrently or, preferably, cocurrently with the drops of liquid through the drying tower. The temperature of a gas at the inlet to the tower is, as a rule, from 60 to 180° C., preferably 100 to 160° C., and at the outlet from the tower is 40 to 100° C., preferably 60 to 90° C. The pressure is, as a rule, in the range from 0.6 to 1.5 bar, and drying under atmospheric pressure is preferred. The resulting solid can be removed from the gas stream in a conventional way, for example by a cyclone or filter bags. This results in a free-flowing powder with a residual solvent content <7.5% of the weight of the finished polymer complex. The particle size in the resulting powder is generally from 10 to 150 $\mu$m, while particle sizes of up to 450 $\mu$m may be obtained on spray granulation.

Another embodiment of the complexes according to the invention comprises reacting the insoluble forms of the N-vinyllactam polymers in a fluidized bed with hydrogen peroxide and the active substance c) with or without the metal salt or metal colloid d). The metal component can also be mixed with the hydrogen peroxide solution beforehand in this case too.

In another embodiment, the complexes used according to the invention have a shell-like structure. This shell-like structure is achieved by applying the abovementioned constituents a), b) and c), with or without d), successively to a solid carrier in the combination or sequence necessary for the required structure, in a suitable apparatus, for example a coating pan or fluidized bed granulator. These processes are also known in principle to the skilled worker. This solid carrier comprises inorganic oxides such as titanium dioxide, aluminum oxide, silicon dioxide, silicates, aluminosilicates, organic carrier materials such as cellulose, starch, insoluble polymers, preferably those suitable for complex formation with hydrogen peroxide, in particular those based on polyvinyllactams. The last-mentioned carrier can also be used as component b) in the preparation of the complexes according to the invention.

The polymer complexes with a layered structure according to the invention are prepared by spraying solutions or suspensions of components a) and c), with or without b) and/or d), onto the carrier in one of the abovementioned apparatuses under the conditions described for the polymer complex powders. This procedure can be repeated if necessary until the required ratios of concentrations of the components are reached. The components can be sprayed on through multicomponent nozzles simultaneously or else successively in any sequence.

If the release of the hydrogen peroxide, the active substances c) and the metal is to be pH-dependent, the complexes can be coated with a polymeric film-former which dissolves or swells at a particular pH. Initiation of release both in acidic and in alkaline medium is possible via suitable choice of these film formers. In the case of complexes with a shell-like structure, these film formers can also delimit the individual layers from one another so that, for example, there is release of active substance from a first layer at a neutral pH and from an inner layer only above or below a particular pH. Suitable polymeric film formers are known in pharmaceutical technology. Examples thereof are hydroxypropylcellulose, hydroxypropylmethylcellulose, vinylpyrrolidone/vinyl acetate copolymers, cellulose acetate phthalate, hydroxypropylmethylcellulose phthalate, shellac, copolymers of acrylic acid or methacrylic acid with (meth) acrylic esters, e.g. copolymers of ethyl acrylate and methacrylic acid (e.g. Kollicoat® MAE 30D, or Eudragits®) or copolymers of dimethylaminomethacrylic acid with neutral methacrylic esters.

Preferred embodiments of the complexes according to the invention have the following structures:

core: polymer b) with component a); shell: polymer b) with component c), with or without component d);

core: polymer b) with component a); shell 1: polymeric film former (see above); shell 2: polymer b) with component c), with or without component d);

core: polymer b) with components a) and d); shell 1: polymeric film former (see above); shell 2: polymer b) with component c), with or without d).

It is possible in the preparation of the polymer complexes according to the invention, whether as polymer powder or as shell-like granules, for further constituents to be present to simplify the processing of the polymer complexes according to the invention or extend their range of action. For example, surfactants can be added, and then remain in the complex, in the preparation of the complexes according to the invention. These may increase the effect of the actual hydrogen peroxide/metal/polymer disinfectant system in contact with germs, and act as solubilizers or wetting agents. Suitable surfactants may be cationic, anionic or nonionic in nature. Examples thereof are sodium dodecyl sulfate, dodecyltrimethylammonium bromide, dimethylalkylbenzylammonium chloride, polysorbate fatty acid esters and ethoxylated mono-, di- and trialkylphenols (EO degree: 3 to 50, alkyl radical: $C_4$–$C_9$), ethoxylated fatty alcohols (EO degree: 3 to 50, alkyl radical $C_8$–$C_{36}$), and alkali metal and ammonium salts of alkyl sulfates (alkyl radical: $C_8$–$C_{12}$), of sulfuric monoesters of ethoxylated alkanols (EO degree: 4 to 30, alkyl radical: $C_{12}$–$C_{18}$) and ethoxylated alkylphenols (EO degree: 3 to 50, alkyl radical: $C_4$–$C_9$), of alkylsulfonic acids (alkyl radical: $C_{12}$–$C_{18}$) and of alkylarylsulfonic acids (alkyl radical: $C_9$–$C_{18}$). Preferred emulsifiers are sodium dodecyl sulfate and polysorbate fatty acid esters.

The described polymer complexes can be stored as solids at room temperature over a lengthy period without loss of hydrogen peroxide. They are inert toward most formulation ingredients used in pharmacy. There are thus no restrictions on their formulation in topical compositions. The formulation ingredients used are the usual pharmaceutical or cosmetic excipients and auxiliaries appropriate for the required type of preparation.

Examples of formulation ingredients which can be used are alcohols such as ethanol, propanol, isopropanol, phenoxyethanol, phenoxy-1- and phenoxy-2-propanol, polyols such as propylene glycol, glycerol or polyethylene glycols, silicones, esters or glycerides of fatty acids, for example isopropyl myristate, myricyl cerotate, cetyl palmitate, glycerides of palmitic acid, stearic acid, linoleic acid, linolenic acid or oleic acid, phospholipids such as cephalins or lecithins, starches, modified starches or hydrocarbons, for example petrolatum or paraffins. The formulations may additionally contain ingredients necessary for their preparation, e.g. the abovementioned surfactants.

Examples of formulations suitable for topical administration of said compositions are dusting powders, ointments, cremes, gels or sprays for the prophylaxis of bacterial infections of skin, e.g. in wound management, or the treatment of bacterial infections of skin, for example in acne vulgaris. The compositions according to the invention can furthermore be formulated in the form of antibacterial lip salves. When soluble complexes are used, they can be converted into films together with adhesives for plasters. The plasters produced in this way have a depot disinfectant effect. Since the compositions according to the invention usually contain starting materials accepted in pharmacy, there are no objections to their use in human medicine.

EXAMPLES

Starting material used stabilized hydrogen peroxide: 50% by weight aqueous solution, stabilized with 0.082% by weight of colloidal silver; commercial product from Hungerbach GmbH, Mörsdorf polyvinylpyrrolidone K30: K value 30 according to H. Fikentscher, Cellulose-Chemie 13 (1932) 18, 71; commercial product from BASF AG crosslinked polyvinylpyrrolidone: Crospovidone®, commercial product from BASF AG polyvinyl caprolactam: K value 30 vinylimidazorl/vinylpyrrolidone copolymer (VI/VP=9:1) produced in the following manner: a mixture of 9 parts of N-vinylimidazole (VI), 1 part of N-vinylpyrrolidone (VP), 0.3 parts of N,N'-divinylimidazolidone, 100 parts of water and 0.1 parts of sodium hydroxide solution (5% strength) was introduced into a stirred vessel equipped with a condenser and was heated to 70° C. while adding of 0.1 parts of a crosslinked polymerisate with a little capabilty of swelling on the basis of VI and/or VP under nitrogen atmosphere. At this temperature the mixture was polymerized for 6 h. The precipitation polymerisate obtained was filtered off, thoroughly washed with water, and dried at 60° C. A white, granulous product was obtained with a yield of 96.5% ethylacrylate/methacrylic acid copolymer (EA/MAS: 1/1): Kollicoat MAE30 D; commercial product from BASF AG.

Analyses

The hydrogen peroxide content of the polymer complexes according to the invention was determined by titration against potassium permanganate. The metal content in the polymer complexes according to the invention was determined by atomic absorption spectrometry. The water content of the polymer complexes was determined by Karl-Fischer titration.

Homogenous polymer hydrogen peroxid silver complexes (Examples 1–3)

Example 1

Preparation by Spray Drying

A solution of 500 g of polyvinylpyrrolidone K30

153 g of hydrogen peroxide (50% by weight aqueous solution, stabilized with 0.126 g of colloidal silver) and 1347 g of water was atomized in a drying tower (d 900 mm; h 1400 mm) by means of a two-fluid nozzle at a pressure of 1.5 bar. Drying took place by means of nitrogen at 1 bar and a tower input temperature of 160° C. and a tower output temperature of 70° C. The resulting powder was separated from the stream of gas by means of a cyclone separator. The obtained powder had a peroxide content of 12.9% by weight, a silver content of 0.019% by weight and a water content of 3% by weight.

Example 2
Preparation by Spray Drying 150 g of polyvinylpyrrolidone and 5.6 g of silver nitrate were dissolved in 500 ml of ethanol and refluxed for 60 minutes. Then, 60 g of a 25% by weight aqueous hydrogenperoxide solution were added. The resulting solution was spray-dried as described in example 1. The powder obtained had a peroxide content of 8% by weight, a silver content of 1.9% by weight and a solvent content of 1% by weight.

Example 3
Preparation by Fluidized Bed Drying

Preparation by fluidized bed drying is carried out in a granulating cylinder which is closed at the bottom by a perforated plate, the upper side thereof provided with a sieve (mesh width 10–500 μm) and at the top by 4 filter bags which are blown free by compressed air every 15 sec. 28 cm above the sieve plate there is a two-component nozzle directed towards the sieve plate. The hydrogen peroxide solution is metered by a peristaltic pump with addition rates of 2.5 to 100 g/min/1000 g of polymer. The amount of polymer used is 100 to 4000 g. The gas throughput is controlled by an outlet air valve and is 120 $m^3$/1 hour to 150 $m^3$/hour. Nitrogen is used as process gas. The inlet air temperature is in the range from 25 to 80° C., and the outlet air temperature is in the range from 25 to 70° C.

250 g of polyvinylcaprolactam were introduced into the granulating cylinder at a stream of gas of 120 $m^3$/h and at 50° C. sprayed (10 g/min) with 153 g of a 50% by weight aqueous hydrogen peroxide solution containing 0.126 g of colloidal silver. Drying was carried out in a stream of gas (150 $m^3$/h; 20 min). The peroxide content of the obtained powder was 23% by weight, the silver content was 0.035% by weight and the water content was 1% by weight.

Core-shell polymer hydrogen peroxide silver complexes (examples 4 to 9)

Example 4
VI/VP Hydrogen Peroxide Silver Complex 200 g of an insoluble VI/VP polymerisate were introduced into a fluidization granulator as in example 3 and, at 60° C., sprayed with 25 ml portions in 4 periods and then with 50 ml portions in 3 periods of a 20% by weight hydrogenperoxide (20 ml/min). Drying in a stream of gas was carried out for 5 min between each of the spraying periods. In a similar manner, the obtained polymer hydrogenperoxide complex was sprayed with 250 ml of an aqueous silver colloid suspension with a silver content of 0.16% by weight. The obtained complex had a peroxide content of 16.8% by weight, a silver content of 0.196% by weight and a water content of 3.7% by weight.

Example 5
Polymer Hydrogenperoxide Silver Complex with Film Forming Agent 100 g of crosslinked polyvinylpyrrolidone were at first sprayed with 200 ml of a 15% by weight hydrogenperoxide solution as in example 4. The obtained polymer hydrogenperoxide complexes were sprayed in 4 portions with a solution of 15 g of Kollicoat MAE30 D., 2 g of triethylcitrate and 0.1 g of colloidal silver in 100 g of water and then dried as in example 3. The obtained complex had a peroxide content of 18% by weight, a silver content of 0.06% by weight and a water content of 2% by weight. Silver and hydrogenperoxide were set free at a pH of 5.5.

Example 6
Polymer Hydrogenperoxide Silver Complex with Film Forming Agent 100 g of crosslinked polyvinylpyrrolidon were sprayed with 200 ml of a 15% by weight hydrogenperoxide solution as in example 4. The obtained polymer hydrogenperoxide complexes were sprayed with a solution of 15 g of Kollicoat MAE30 D and 2 g of triethylcitrate in 4 portions. Then they were sprayed with a solution of 0.1 g of colloidal silver in 100 ml of water and dried as in example 3.

Example 7
Polymer Hydrogenperoxide Silver Complex with Film Forming Agent

The procedure of example 6 was repeated but instead of the silver colloid a 0.1% by weight solution of silver nitrate was used. The silver content in the obtained complex was 0.04% by weight.

Example 8
Polymer Hydrogenperoxide Lactic Acid Complex with Film Forming Agent 100 g of crosslinked polyvinylpyrrolidone were introduced into a granulating cylinder (see above) and, at 60° C., sprayed with 20 ml portions in four periods and then with 40 ml portions in three periods of a 15% by weight aqueous hydrogen peroxide solution (20 ml/min). Drying in a stream of gas (150 $m^3$/hour; 60° C.) was carried out for 5 min between each of the spraying periods.

Subsequently, a solution of 15 g of Kollicoat®MAE30D in 100 ml of water was sprayed on in four portions and again dried for 20 min. After this, a solution of 1 g of lactic acid in 100 ml of water was sprayed in 4 potions and again dried.

The resulting polymer complex had a hydrogen peroxide content of 19% by weight and a water content of 1% by weight.

Example 9
Polymer Hydrogenperoxide Silver Complex with Film Forming Agent

Example 8 was repeated, but 200 ml of a 15% by weight hydrogenperoxide solution stabilized with 0.025% by weight silver were used.

The hydrogenperoxide content of the obtained product was 20% by weight, the silver content was 0.024% by weight and the water content was 1.5% by weight.

Formulations, of the polymer complexes according to the invention (examples 10 to 14)

Components used polyacrylic acid: Carbopol® C981; commercial product from BF Goodrich Chemical ethyleneoxide/propyleneoxide block copolymer (EO/PO: 70/30) $M_n$ 9840 to 146000; Lutrol® F 127 of BASF AG polyethylene glycol: $M_n$ 400; Lutrol® E 400 of BASF AG polyethylene glycol: $M_n$ 4000; Lutrol® E 4000 of BASF AG silicone oil: density ρ (25° C.) 0.95 g/$cm^3$, viscosity (25° C.) 2.5 $mm^2$/s, Dow Corning Fluid 344 (cyclic tetradimethyl siloxane of Dow-Corning)

starch diphosphate on the basis of corn starch: Mais $PO_4$ 100 K (phosphate content: <0.1% by weight in solids); commercial product of Hauser KG

Example 10
Formulation in the Form of a Tooth Paste 10 g of the complex produced according to example 1 were dissolved in 78 g of water and mixed with 2 g of Carbopol® and 10 g of 1,2-propylene glycol in a vacuum homogenizer to give a bubble free gel.

Example 11
Gel for use in Skin Disinfection 10 g of the complex from Example 1, 75 g of water, 5 g of 1,2-propylene glycol and 20 g of Lutrol® F 127 were mixed, at below 10° C., in the manner described in example 6 to form a gel.

Example 12
Formulation in the Form of a Salve 20 g of the complex of example 1 were dissolved in a mixture of 50 g of Lutrol® E 400 and 5 g of water and heated to 55–60 ° C. Subsequently, at this temperature 25 g of Lutrol® E 4000 were added while stirring and then the formulation was allowed to cool while stirring.

Example 13
Formulation in the Form of a Concentrate for use as a Mouth Rinse 25 g of the complex of example 1 were dissolved in a mixture of 1 g of 1,2-propylene glycol, 9 g of ethanol and 65 g of water.

Example 14
Formulation as Spray Powder 2.5 g of the complex of example 1 were micronized using a micronizer and introduced into a pressurized vessel together with 1 g of silicone oil (see above) and 2.5 g of corn starch diphosphate. Subsequently the vessel was filled with 5 g of pentane and 2.2 g of propane/butane.

We claim:

1. A composition comprising, in addition to conventional auxiliaries, an effective amount of at least one polymer complex consisting essentially of
   a) from 0.5 to 30% by weight, based on the weight of said polymer complex, of hydrogen peroxide,
   b) from 50 to 99.5% by weight, based on the weight of said polymer complex, of at least one N-vinyllactam homo- or copolymer,
   c) from 0 to 15% by weight, based on the weight of said polymer complex, of a therapeutically active compound different from a) and d), and
   d) from 0.01 to 15% by weight, based on the weight of said polymer complex, of a colloidal metal or a metal salt wherein the metal is Ag,
which composition is adapted for topical application for prophylaxis or for treatment of a bacterial or viral infection of skin, and which is obtained by mixing an effective amount of a powder of the polymer complex with the conventional auxiliaries, which powder of the polymer complex is obtained
   i. by subjecting a solution of the N-vinyllactam polymer together with a hydrogen peroxide solution and a metal salt solution or a dispersion of the colloidal metal and optionally a solution comprising component c) to spray drying, spray-granulating or drying in a fluidized bed, or
   ii. by reacting the N-vinyllactam polymer with hydrogen peroxide and a metal salt solution or a suspension of the colloidal metal in a fluidized bed.

2. The composition defined in claim 1, wherein the N-vinyllactam polymer b) is composed of
   20–100% by weight of at least one N-vinyllactam,
   0–80% by weight of at least one copolymerizable monoethylenically unsaturated monomer, and
   0–20% by weight of at least one crosslinking monomer.

3. The composition defined in claim 1, wherein the N-vinyllactam homo- or copolymer is selected from homo- and copolymers of N-vinylpyrrolidone, N-vinylpiperidone, N-vinylcaprolactam, N-vinyl-3-morpholinone, and N-vinyl-4-oxazolidinone.

4. The composition defined in claim 1, wherein component b) is a homo- or copolymer of N-vinylpyrrolidone or of N-vinylcaprolactam with a K value of from 10 to 110.

5. The composition defined in claim 1, wherein component c) is selected from the group consisting of aldehydes, α-hydroxy carboxylic acids, polyhydroxylated aromatic compounds and hydroxyarylcarboxylic acids.

6. The composition defined in claim 1, wherein component d) is a silver salt or colloidal silver.

7. The composition defined in claim 1, wherein the powder of the polymer complex is obtained by subjecting a solution of the N-vinyllactam polymer together with a hydrogen peroxide solution and a metal salt solution or a dispersion of the colloidal metal and optionally a solution comprising component c) to spray drying, spray-granulating or drying in a fluidized bed.

8. The composition defined in claim 1, wherein the powder of the polymer complex is obtained by reacting the N-vinyllactam polymer with hydrogen peroxide and a metal salt solution or a suspension of the colloidal metal in a fluidized bed.

9. The composition defined in claim 1, wherein the powder of the polymer complex is obtained by applying a hydrogen peroxide solution, a solution of the N-vinyllactam and a metal salt solution or a dispersion of the colloidal metal to a solid carrier.

10. The composition defined in claim 1, wherein the polymer complex comprises at least 5% by weight of hydrogen peroxide.

11. The composition defined in claim 1, wherein the N-vinyllactam polymer b) has a solubility in water at 20° C. of at least 0.5 g polymer per 100 ml of water.

12. The composition defined in claim 2, wherein the N-vinyllactam polymer b) comprises from 0.02 to 15 mol-%, based on the monomers, of the crosslinking monomers.

13. The composition defined in claim 2, wherein the N-vinyllactam polymer b) comprises from 0.05 to 3 mol-%, based on the monomers, of the crosslinking monomers.

14. The composition defined in claim 1, which is in form of a powder, an ointment, a cream, a gel or a liquid.

* * * * *